（12）United States Patent
Kramer et al.

(10) Patent No.: US 10,708,473 B2
(45) Date of Patent: Jul. 7, 2020

(54) OCULAR IMAGING WITH ILLUMINATION IN IMAGE PATH

(71) Applicant: Verily Life Sciences LLC, South San Francisco, CA (US)

(72) Inventors: Ryan Kramer, San Francisco, CA (US); Eliezer Glik, San Francisco, CA (US); Honglei Wu, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 9 days.

(21) Appl. No.: 16/191,938

(22) Filed: Nov. 15, 2018

(65) Prior Publication Data

US 2019/0199893 A1 Jun. 27, 2019

Related U.S. Application Data

(60) Provisional application No. 62/609,956, filed on Dec. 22, 2017.

(51) Int. Cl.
*H04N 5/225* (2006.01)
*G02B 27/10* (2006.01)
(Continued)

(52) U.S. Cl.
CPC ............ *H04N 5/2252* (2013.01); *A61B 3/14* (2013.01); *G02B 21/367* (2013.01); *G02B 27/10* (2013.01);
(Continued)

(58) Field of Classification Search
CPC ............... H04N 5/2252; H04N 5/2256; H04N 5/23212; H04N 5/232133; H04N 5/2354;
(Continued)

(56) References Cited

U.S. PATENT DOCUMENTS

| 4,834,528 A | 5/1989 | Howland et al. |
| 6,733,129 B2 | 5/2004 | Masaki |

(Continued)

FOREIGN PATENT DOCUMENTS

| EP | 0700266 B1 | 1/2003 |
| JP | 2017099717 A | 6/2017 |

OTHER PUBLICATIONS

Fan et al., "Modeling Transient Pupillary Light Reflex Induced by a Short Light Flash," IEEE Transactions on Biomedical Engineering, vol. 58, No. 1, Jan. 2011, pp. 36-42.
(Continued)

*Primary Examiner* — Abdelaaziz Tissire
(74) *Attorney, Agent, or Firm* — Christensen O'Connor Johnson Kindness PLLC

(57) ABSTRACT

An apparatus for imaging an interior of an eye includes a light sensitive sensor, and a housing structure with an opening defining an imaging area to place the eye for imaging by the light sensitive sensor. One or more light emitters (LEs) are disposed in an image path between the light sensitive sensor and the eye during capture of a plurality of images. A controller is coupled to the plurality of LEs and the light sensitive sensor. The controller implements logic that when executed by the controller causes the apparatus to perform operations including: illuminating the imaging area with the one or more LEs; and capturing, with the light sensitive sensor, the plurality of images of the interior of the eye at the same time as the eye is illuminated with the light from the one or more LEs.

26 Claims, 10 Drawing Sheets

(51) Int. Cl.
*H04N 5/232* (2006.01)
*A61B 3/14* (2006.01)
*G02B 21/36* (2006.01)

(52) U.S. Cl.
CPC ....... *H04N 5/2256* (2013.01); *H04N 5/23212* (2013.01)

(58) Field of Classification Search
CPC ................ H04N 1/624; H04N 5/2355; H04N 5/355–3559; G02B 21/367; G02B 27/10; G06T 2207/30216; G06T 5/007–009; G06T 2207/20208; G06K 9/00597–00617; A61B 3/14; A61B 3/12
See application file for complete search history.

(56) References Cited

U.S. PATENT DOCUMENTS

| | | | |
|---|---|---|---|
| 7,458,685 | B2 | 12/2008 | Liang et al. |
| 7,499,634 | B2 | 3/2009 | Yogesan et al. |
| 7,878,653 | B2 | 2/2011 | Ichikawa et al. |
| 7,954,949 | B2 | 6/2011 | Suzuki |
| 8,109,635 | B2 | 2/2012 | Allon et al. |
| 8,408,464 | B2 | 4/2013 | Zhu et al. |
| 8,514,277 | B2 | 8/2013 | Dyer |
| 8,684,529 | B2 | 4/2014 | Johansson et al. |
| 8,811,657 | B2 | 8/2014 | Teiwes et al. |
| 8,955,971 | B2 | 2/2015 | Ichikawa et al. |
| 9,078,599 | B2 | 7/2015 | Yogesan et al. |
| 9,125,559 | B2 | 9/2015 | Kersting et al. |
| 9,271,646 | B2 | 3/2016 | Neal et al. |
| 9,289,122 | B2 | 3/2016 | Chinnock et al. |
| 9,498,126 | B2 | 11/2016 | Wang |
| 9,918,629 | B2 | 3/2018 | Wang |
| 2009/0153797 | A1* | 6/2009 | Allon .................. A61B 3/12 351/206 |
| 2010/0097573 | A1* | 4/2010 | Verdooner ............ A61B 3/14 351/206 |
| 2010/0128117 | A1* | 5/2010 | Dyer ................. G06K 9/00604 348/78 |
| 2012/0169995 | A1* | 7/2012 | Mohr ................... A61B 3/12 351/206 |
| 2013/0010259 | A1 | 1/2013 | Carnevale |
| 2013/0057828 | A1 | 3/2013 | de Smet |
| 2013/0083184 | A1* | 4/2013 | Yogesan ............ A61B 3/0033 348/78 |
| 2013/0194548 | A1 | 8/2013 | Francis et al. |
| 2013/0208243 | A1 | 8/2013 | Sakagawa |
| 2013/0329189 | A1 | 12/2013 | Mizucchi |
| 2014/0240666 | A1 | 8/2014 | Ootsuki |
| 2014/0268040 | A1* | 9/2014 | Mujat ................. A61B 3/102 351/206 |
| 2016/0174838 | A1 | 6/2016 | Herranen et al. |
| 2016/0302665 | A1 | 10/2016 | Swedish et al. |
| 2016/0317031 | A1 | 11/2016 | Yang et al. |
| 2016/0338589 | A1 | 11/2016 | Carrasco-Zevallos et al. |
| 2016/0366317 | A1* | 12/2016 | Ivanisov ............ G06K 9/00604 |
| 2017/0103261 | A1* | 4/2017 | Rauhala ............ G06K 9/00597 |

OTHER PUBLICATIONS

Bengtsson et al., "A new generation of algorithms for computerized threshold perimetry, SITA," ACTA Ophthalmologica Scandinavica 1997, vol. 75, pp. 368-375.

Sugita et al., "Motion artifact and speckle noise reduction in polarization sensitive optical coherence tomography by retinal tracking," Biomedical Optics Express, vol. 5, No. 1, pp. 106-122.

Tran et al., Construction of an Inexpensive, Hand-Held Fundus Camera through Modification of a Consumer "Point-and-Shoot" Camera, Investigative Ophthalmology & Visual Science, Nov. 2012, vol. 53, No. 12, 10 pages.

De Matos et al., "Coaxial fundus camera for ophthalmology," Proc. of SPIE, vol. 9578, 2015, 5 pages.

Dehoog et al., "Optimal parameters for retinal illumination and imaging in fundus cameras," Applied Optics, vol. 47, No. 36, pp. 6769-6777.

TRC-NW8 Non-Mydriatic Retinal Camera, Topcon Medical Systems, Inc., http:www.topconmedical.com/products/trcnw8.htm, Accessed Aug. 31, 2016, 1 page.

CenterVue Homepage, http://www.centervue.com/, Accessed Aug. 31, 2016, 5 pages.

Swedish et al., "eyeSelfie: Self Directed Eye Alignment using Reciprocal Eye Box Imaging," MIT Media Lab—Camera Culture Group, http:web.media.mit.edu/~tswedish/projects/eyeSelfie.html, Accessed Aug. 31, 2016, 3 pages.

International Search Report and Written Opinion from the International Searching Authority dated Apr. 18, 2019 for International Application No. PCT/US2018/066594, filed Dec. 19, 2018, 9 pages.

\* cited by examiner

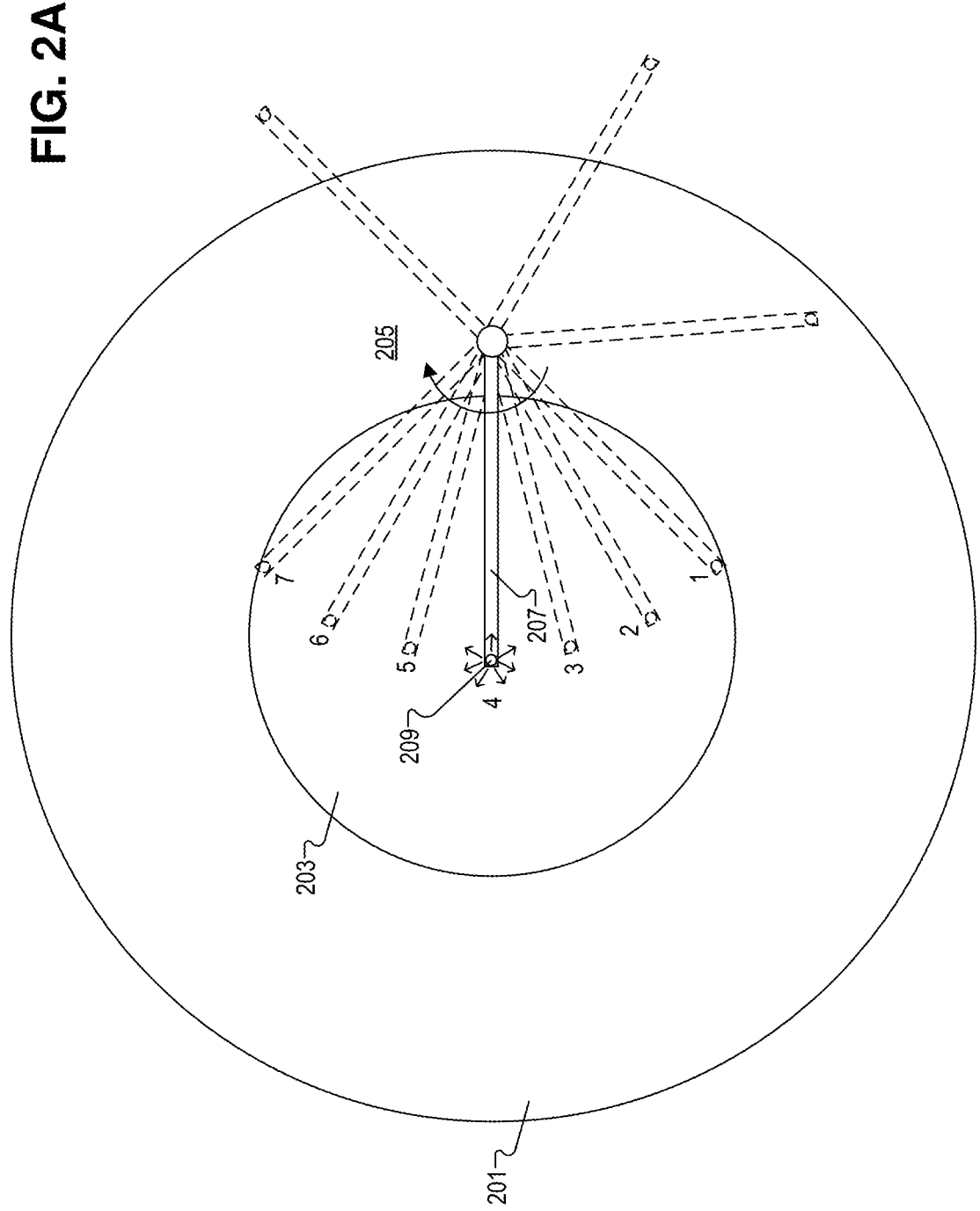

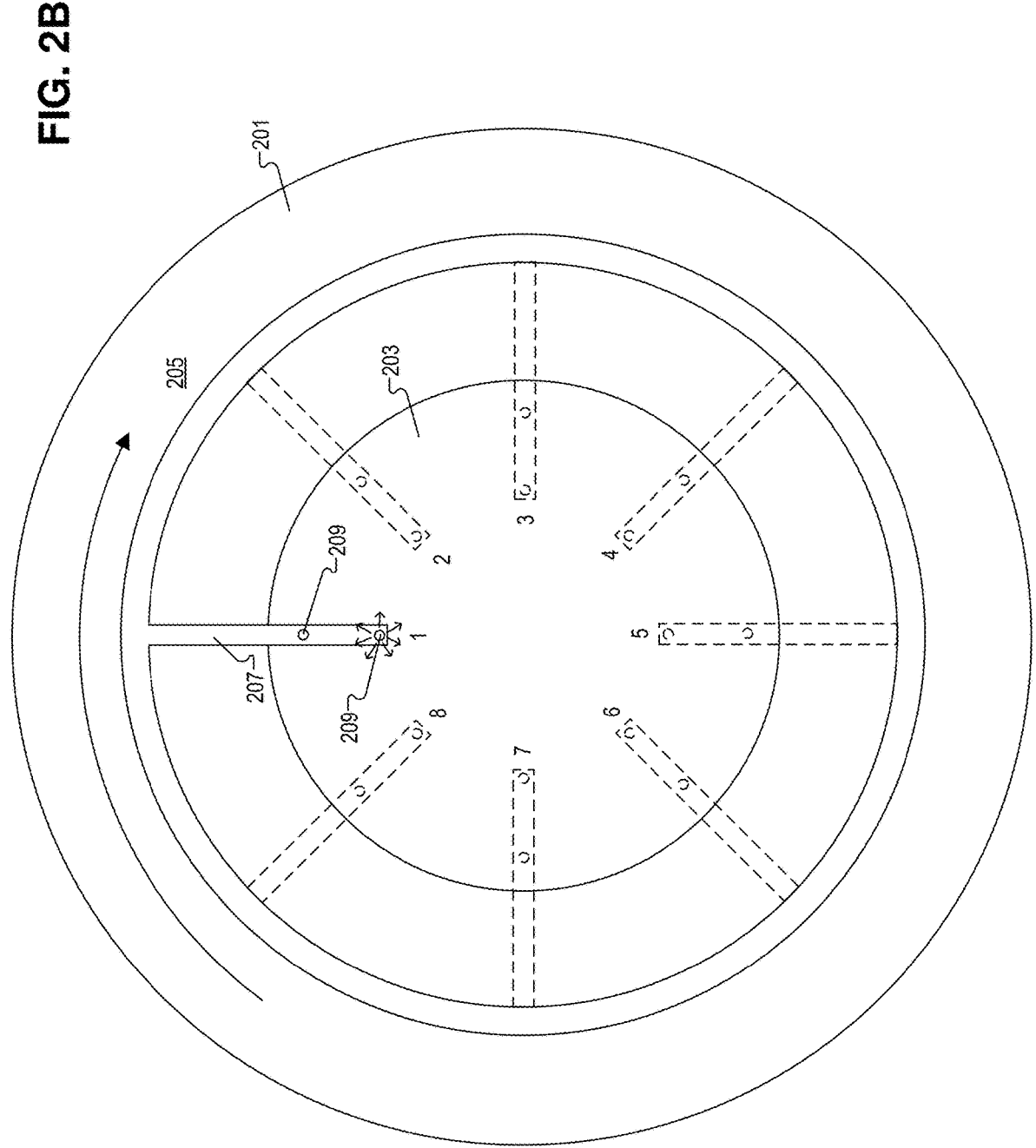

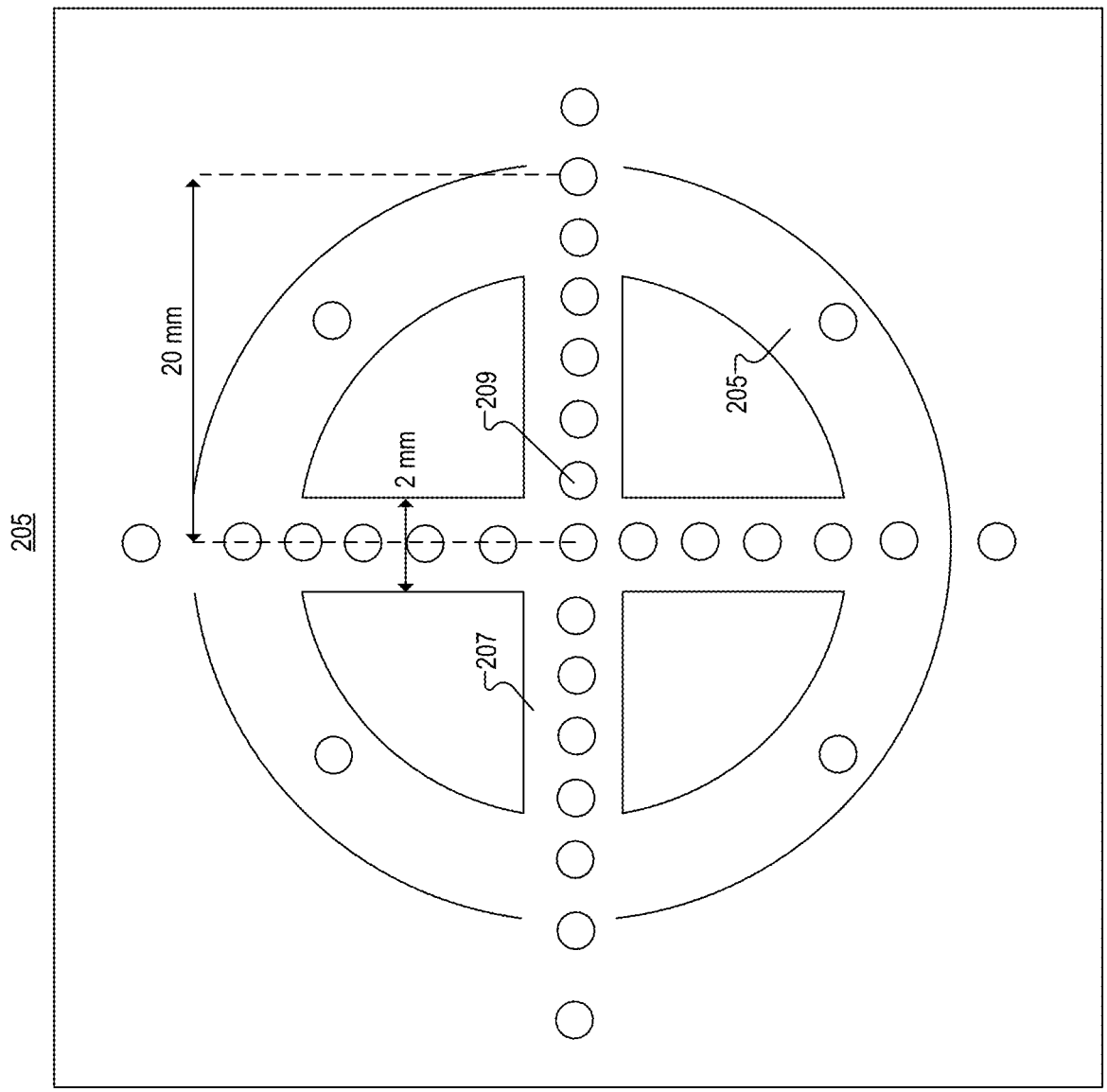

OCULAR IMAGING WITH ILLUMINATION IN IMAGE PATH

REFERENCE TO RELATED APPLICATION

This application claims the benefit of U.S. Application No. 62/609,956, filed on Dec. 22, 2017, the contents of which are incorporated herein by reference.

TECHNICAL FIELD

This disclosure relates generally to imaging technologies, and in particular, relates to retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity while often creating optical aberrations or image artifacts, such as lens flare. Lens flare is a phenomenon where light scatters off of interior components of a lens system due to internal reflections, refractive index changes at various internal boundaries, imperfections, or otherwise. This scattered light shows up in the retinal image as lens flare, which is deleterious to the image quality. The brighter the illumination, the more pronounced the lens flare, which undermines the goal of improving image fidelity. Other image artifacts may arise due to corneal reflections or iris reflections from misalignment with the pupil.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 2A-2D illustrate dynamic illuminators that may be included in the apparatus of FIGS. 1A-1B, in accordance with embodiments of the disclosure.

DETAILED DESCRIPTION

Embodiments of an apparatus and method for ocular imaging with an illumination source in the image path are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Bright illumination is a double edge sword. It improves the fidelity of a retinal image while creating optical aberrations (e.g., cornea reflection/flare). Some cameras may have a ring shaped illumination source/annular light emitter. These cameras may have an illumination aperture with a diameter small enough, relative to the diameter of the annular light source, such that most (if not all) of the cornea reflections are blocked. Conventional cameras may take a single still image per patient. Accordingly, a cornea reflection would be unacceptable because it ruins the retinal image of the patient. To solve this problem, embodiments of the disclosure presented here provide for the focal stacking of retinal images. However, even when using a multi-image stacking technique to create a composite high-fidelity image, a spatially static illumination source may need a very small aperture. Thus embodiments of the instant disclosure include designs for a dynamic illuminator (which is disposed in the image path and may be stationary or mobile) that remedies these deficiencies. Moreover, by placing the dynamic illuminator in the image path (e.g., the path of light traveling from the eye, or imaging area, to the camera) it is possible to achieve a satisfactory image for an eye that has shifted location. And by using focal stacking, image artifacts resulting from the presence of the dynamic illuminator that appear in the image of the eye may be removed before forming the composite image. These artifacts stem from reflections from the cornea, lens elements, and inner eye scatter.

Figure 1A:
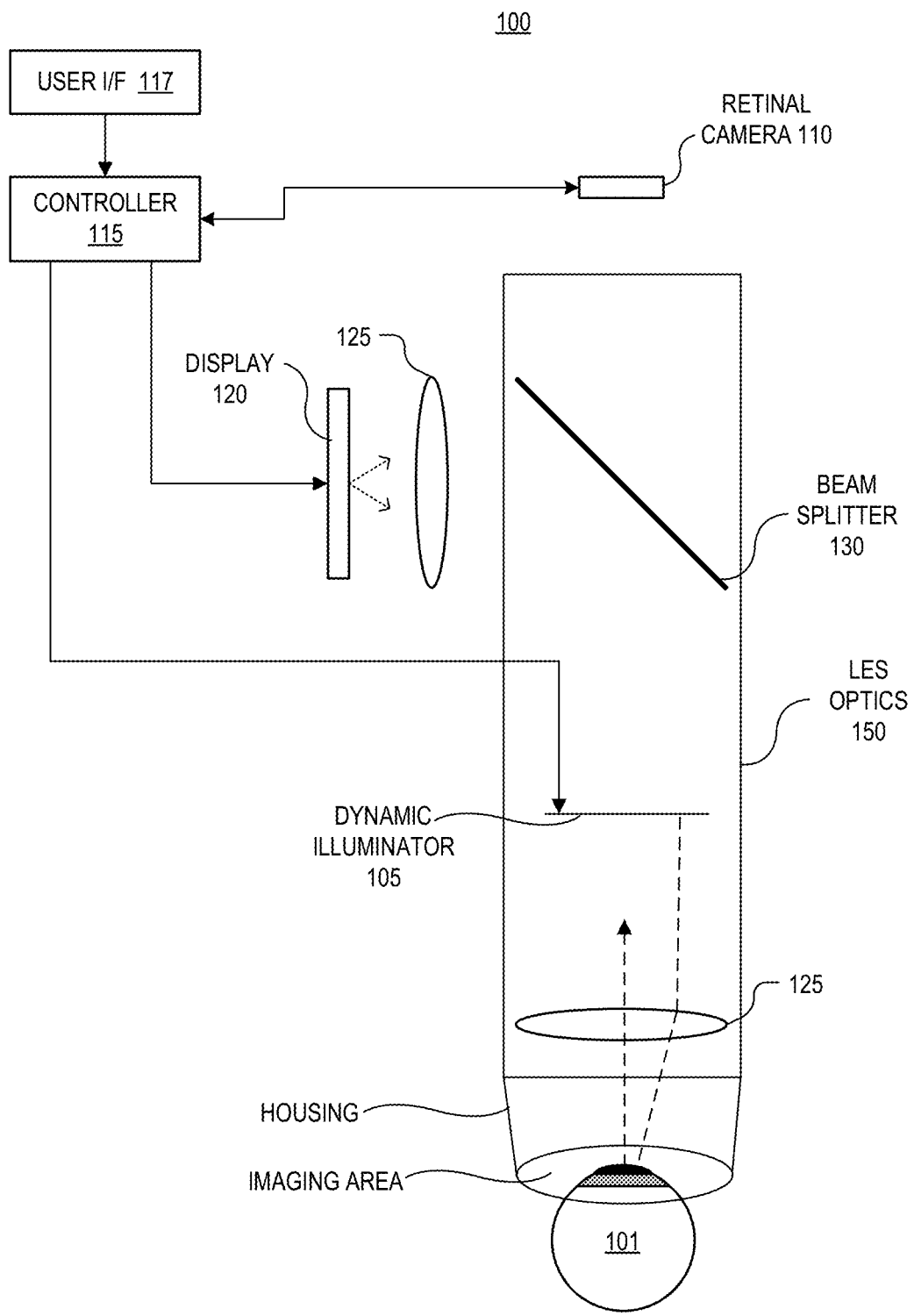
FIGS. 1A-1B illustrate an apparatus for imaging an interior of an eye, in accordance with an embodiment of the disclosure.
Figure 1B:
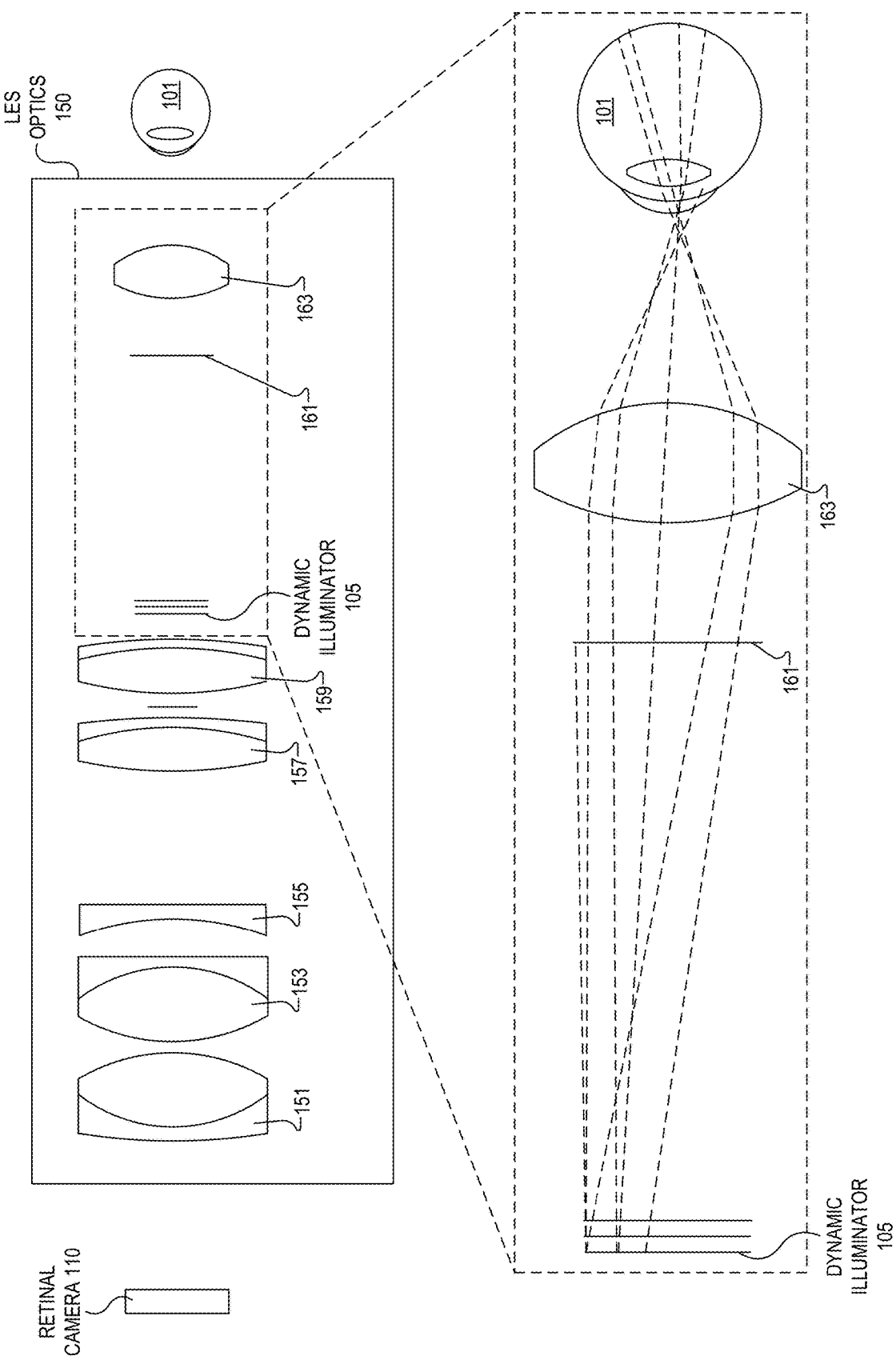

FIGS. 1A-1B illustrates an apparatus for imaging an interior of an eye, in accordance with an embodiment of the disclosure. More specifically, FIG. 1A depicts the apparatus, while FIG. 1B shows a detailed view of lens optics 150 used in apparatus 100. The illustrated embodiment of retinal imaging system 100 includes a dynamic illuminator 105 (which has one or more light emitters (LEs) disposed in/on it), retinal camera 110, controller 115, user interface 117, display 120, and an optical relay system that includes lenses 125 and a beam splitter 130. As shown, the entire apparatus may be disposes in, or include, a housing structure (e.g., plastic or metal structure/casing) with an opening defining an imaging area to place the eye for imaging by camera 110.

In the depicted embodiment, retinal camera 110 includes a light sensitive sensor (e.g., CMOS image sensor, CCD image sensor, or the like). One or more LEs (e.g., visible or infrared light emitting diodes, laser diodes, flash bulbs, or the like) are disposed on dynamic illuminator 105 (part of an illumination system), which is positioned in the image path between retinal camera 110 and the eye during capture of a plurality of images of the retina. Controller 115 (e.g., a general purpose or specialty processor, distributed system, microcontroller, or the like) is coupled to the plurality of LEs and the light sensitive sensor in retinal camera 110, and controller 115 implements logic that when executed by controller 115 causes apparatus 100 to perform a series of operations. For example, apparatus 100 may illuminate eye 101 with the one or more LEs, and capture (with the light sensitive sensor) the plurality of images of the interior of the eye (e.g., the retina) while eye 101 is illuminated with the light from the one or more LEs.

In some embodiments, controller 115 may further implement logic (e.g., in hardware, software, or a combination of the two) that causes the apparatus to combine at least some of the images in the plurality of images to form a composite image of the interior of the eye. In one embodiment, combining may include at least one of focus stacking (i.e., combining multiple images taken at different focus distances to give a resulting image with a greater depth of field than any of the individual source images), image stitching (i.e., combining multiple photographic images with overlapping fields of view to produce a segmented panorama or high-resolution image), image blending (i.e. combining a background image and foreground image giving the appearance of partial transparency), or any combination thereof. One of ordinary skill in the art having the benefit of the present disclosure will appreciate that other techniques may be used in addition to those described here. In one embodiment, eye 101 is illuminated with the one or more LEs from a plurality of positions within the image path. This may be achieved by having multiple stationary LEs located in different positions in the image path or by moving the one or more LEs to different positions during image capture. It is appreciated that the image path may include light reflected from the interior of the eye having a path to be incident on, or directed to, the light sensitive sensor, and that some of this light may be absorbed by dynamic illuminator 105. In some embodiments, dynamic illuminator may include a circuit board with light emitting diodes mounted on the circuit board. In some embodiments, at least part of the structure holding the light emitters (e.g., the illumination system) is substantially transparent (e.g., glass, acrylic, or the like), or capable of turning transparent or substantially transparent (e.g., a liquid crystal based device that can become transparent). Another form of transparency is to position the structure so that it is out of focus and therefore doesn't show up in the plurality of images.

At least part of dynamic illuminator 105 is physically positioned in the optical path of eye 101. As will be shown in FIGS. 2A-2D, the light used to form the retinal images is passed through, or around, dynamic illuminator to retinal camera 210. However, some image light may be absorbed by dynamic illuminator 105 since it is disposed in the image path. In addition to reducing image artifacts due to deleterious reflections from the cornea, the use of multiple illumination positions from dynamic illuminator 105 also serves to increase the eyebox of system 100. The eyebox is the region in space where eye 101 can be located and imaged. One strategy to increase the eyebox employs light coming from the middle (or from other parts) of the imaging aperture, and by obtruding part of the symmetric aperture, it is possible to produce this light. In some embodiments, all of the discrete light sources included in dynamic illuminator 105 are disposed inside a perimeter of the imaging path extending from eye 101 to retinal camera 110, while in other embodiments some light sources (light emitters) are disposed outside the imaging path. In some (mobile) embodiments, the light sources may move in and out of the imaging path, and images may be captured at both illumination positions.

The depicted embodiment includes beam splitter 130 (or polarizing beam splitter) which is positioned to pass a portion of the light of retinal images to retinal camera 110 while reflecting display light output from display 120 to eye 101. The display light may include a fixation target or other visual stimuli to aid retinal alignment during imaging. In some embodiments, beam splitter 130 is more transmissive than reflective. In one embodiment, beam splitter 130 is approximately 90% transmissive and 10% reflective. Other reflectance/transmittance ratios may be implemented. Lenses 125 are provided throughout system 100 to provide image and light focusing in the optical paths. However, as will be shown by FIG. 1B, the lenses depicted here in FIG. 1A are merely a cartoon illustration of a more complex lens system. User interface 117 provides a mechanism to commence burst image capture. In one embodiment, user interface 117 is a button, touch screen, mouse, or the like. Auto capture may also be used based on satisfying a merit based formula during pre-capture.

FIG. 1B depicts a detailed view of lens optics 150 used in apparatus 100, in accordance with an embodiment of the disclosure. It is appreciated that "lens optics 150" may also include optical devices other than lenses such as apertures, beam splitters, or the like. The depicted embodiment includes six discrete lenses (some of which may have multiple components). The bottom figure illustrates ray diagrams of the light emitted from dynamic illuminator 105, and how the light travels into eye 101.

Disposed between dynamic illuminator 105 and eye 101 is aperture 161, and first lens 163, including two convex surfaces. As depicted, aperture 161 is deposed between dynamic illuminator 105 and first lens 163 to block light that could otherwise cause unwanted reflections. Lens 159 has two convex surfaces, and two discrete parts, and is located between lens 157 and dynamic illuminator 105. As shown lens 157 has similar features as lens 159 and is disposed between lens 155 and lens 159. Lens 155 is disposed between lens 157 and 153, and has a concave surface (facing retinal camera 110) and a convex surface (facing dynamic illuminator 105). Lens 153 is disposed between lens 151 and lens 155. One of ordinary skill in the art will appreciate that the lenses and other optical components depicted here represent just one of many ways to assemble the lens optics of system 100, in accordance with the teachings of the present disclosure.

As shown in the magnified bottom figure, depending on the location of the LEs, different artifacts and different illumination profiles may arise in the image depending on the location of the eye in the eyebox and based on the LE's used. By placing the LE into the imaging aperture, it is possible to achieve focus higher in the Y-direction (e.g., direction between top and bottom of page) that may be needed for a shifted eye location in the Y-direction.

FIGS. 2A-2D illustrate dynamic illuminators that may be included in the apparatus of FIGS. 1A-1B, in accordance with embodiments of the disclosure. One of ordinary skill in the art will appreciate that while four embodiments of dynamic illuminators 205 are shown here, these examples are not exhaustive; many other shapes and configurations are possible in accordance with the teachings of the present disclosure. Moreover, any number of designs may be used to optimize the modular transfer function (MTF) of a given optical system.

FIG. 2A depicts an embodiment of dynamic illuminator 205 that may reside in the image path in the device depicted in FIG. 1A. As illustrated, dynamic illuminator 205 is located in front of eye 201 (including pupil 203), and has arm 207 that extends outward from a central point. At the distal end (opposite the central point or rotational axis) of arm 207 is LE 209. It is appreciated that for at least part of the image acquisition process, arm 207 is in the image path (e.g., arm 207 may spin into the image path during image capture).

In operation, the central pivot point may be coupled to a motor (e.g., an electric motor) which may be used to spin or rotate arm 207 (and consequently spin or rotate LE 209 around the pivot point) to a variety of positions (e.g., positions 1-7) relative to the eye. LE 209 may strobe on at a plurality of locations, some of which may be inside the image path between the eye and the camera. The individual/discrete flashes may correspond to image capture of individual/discrete images with the camera. It is appreciated that there may be the same number of flashes (illumination events) as images captured, a greater number of flashes than images captured, or a fewer number of flashes than images captured. Additionally, the pivot point may be stationary or move while arm 207 is spinning. It is appreciated that more than one dynamic illuminator 205 may be employed simultaneously, and arm 207 may include more than one LE 209, in accordance with the teachings of the present disclosure.

FIG. 2B depicts another embodiment of a dynamic illuminator 205 disposed in front of eye 201 (including pupil 203). As shown, dynamic illuminator 205 is substantially ring-shaped (i.e., annular) and arm 207 extends towards the center of the ring. A LE 209 is located on the distal end of the arm (near the center of the ring). As shown dynamic illuminator 205 may rotate so that the LEs 209 move to different positions (e.g., positions 1-8). As shown LEs 209 (e.g., an LED) are fixed at the end, and in the middle of, an arm 207 attached to the ring that spins about the imaging path axis. As the arm (e.g., arm 207) sweeps through the imaging path, a frame is captured with the arm at the first position. The arm/ring continues spinning to the next position where another frame is captured. This continues until all eight frames have been captured, enabling the final stacked image to be uniformly illuminated while removing any incidence of the arm in the individual frames. Like the device in FIG. 1A, this rotation may be achieved using an electric motor coupled to the controller. The camera (or light sensitive sensor) may capture an image at each of the eight locations. While eight locations are depicted here, one of ordinary skill in the art having the benefit of the present disclosure will appreciate that images may be captured when arm 207 is at any number of locations. Although the depicted embodiment has only one arm 207 with two LEs 209, in other embodiments, there may be multiple arms (with one or more LEs) extending towards the center of the ring, or outward from the ring. The arms may be symmetrical or may have different shapes and lengths, in accordance with the teachings of the present disclosure.

Figure 2C:
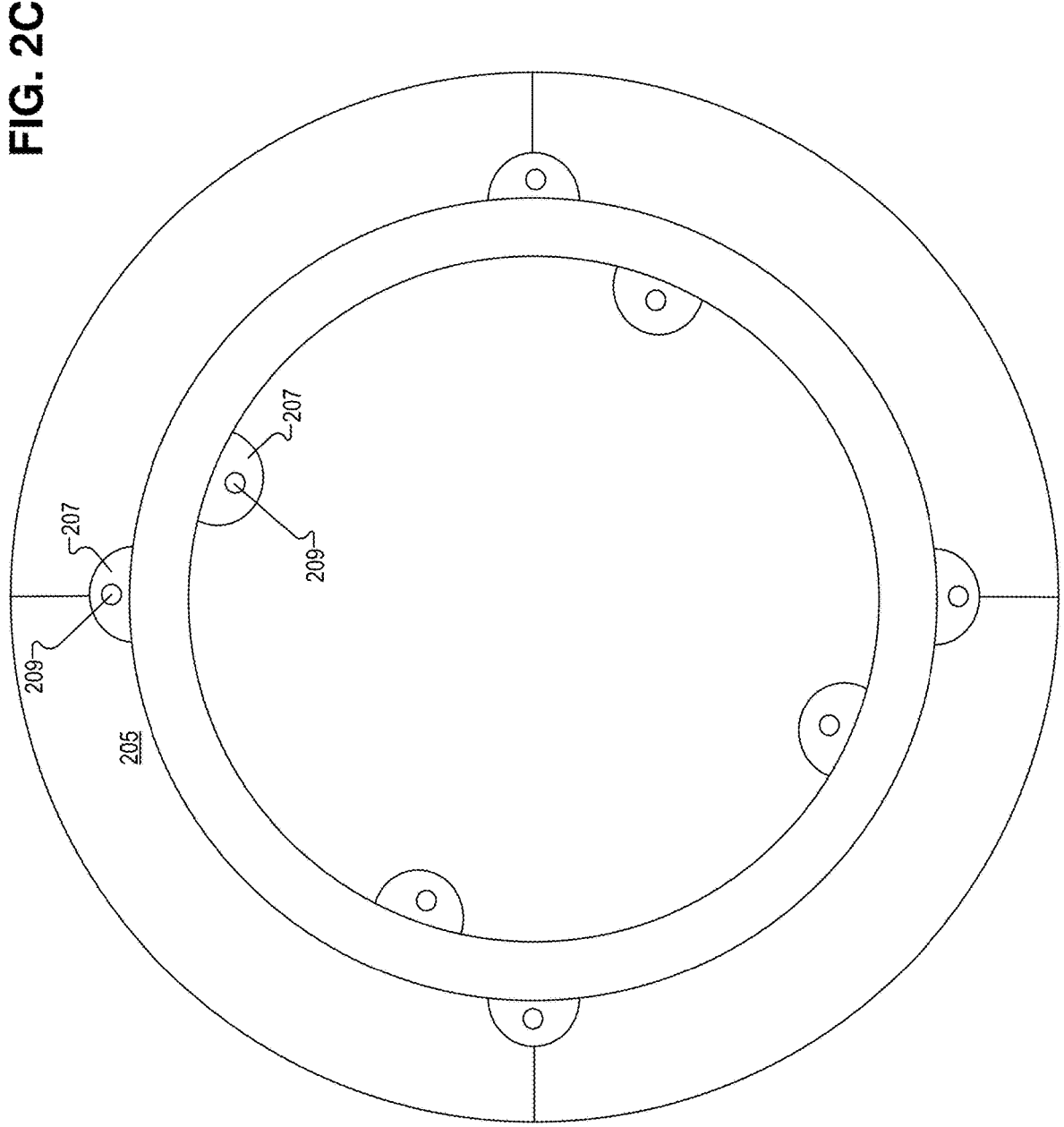

FIG. 2C depicts a stationary dynamic illuminator 205. As shown, some of arms 207 (which here are substantially semicircular) extend toward a center of the ring, and some of arms 207 extend away from the center of the ring. As shown, arms 207 each have a single LE 209. Also, arms 207 are located at substantially π/2 radians around the ring for both arms 207 extending towards the center of the ring, and the arms 207 extending outward from the center of the ring. Like the other embodiments of dynamic illuminator 205, in the depicted embodiment, the stationary dynamic illuminator is at least partially disposed in the image path of light from the retina to the camera. In the depicted embodiment, the clear aperture (where the image light travels through) allows LEs 209 to be placed both inside and around the imaging aperture. One benefit is that the aperture is symmetric in nature, so part of the aperture can be obtruded asymmetrically without obtruding the image.

FIG. 2D depicts another stationary (e.g., arms 207 and LEs 209 are at fixed positions in the image path) embodiment of dynamic illuminator 205. In the depicted embodiment, arms 207 extend toward the center of the image path to form a cross-shaped structure in the image path (the four quadrants created by the cross-shaped structure are empty space, or a transparent material, for image light to pass through). In other embodiments, it is appreciated that there may be any number of intersecting arms such as 2, 3, 5, or the like. As depicted, a plurality of LEs 209 are disposed along arms 207 and around the periphery of the image path. In the depicted embodiment, the LEs 209 may be fired in sequence (e.g., one at a time starting from the LE 209 closest to the upper left hand corner moving down to the lower right hand corner, or the like). Alternatively or additionally, some or all of LEs 209 may be fired simultaneously. One of ordinary skill in the art having the benefit of the present disclosure will appreciate that there are a number of LE illumination patterns that may be employed.

Figure 3:
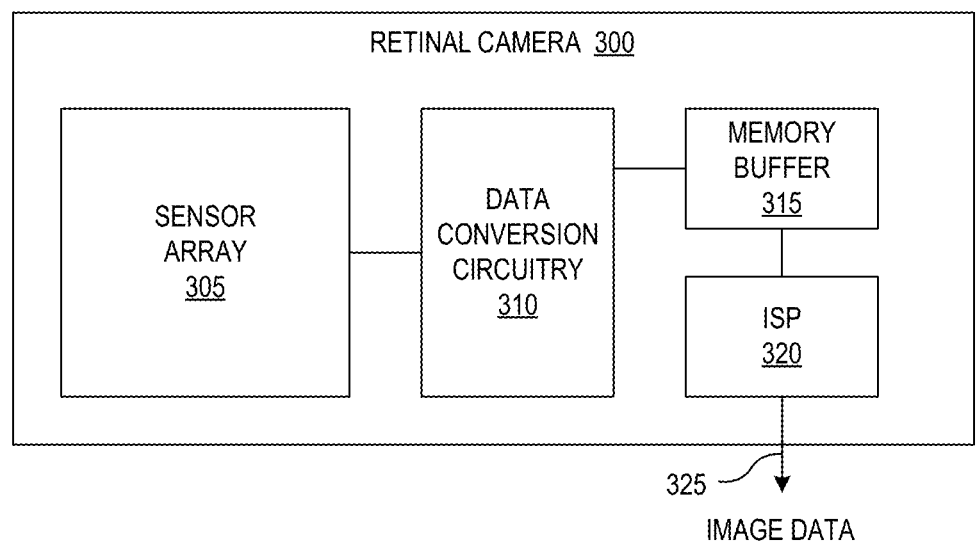
FIG. 3 is a functional block diagram of a retinal camera including an integrated image signal processor, in accordance with an embodiment of the disclosure.

FIG. 3 is a functional block diagram of a retinal camera 300 including an integrated image signal processor, in accordance with an embodiment of the disclosure. Retinal camera 300 is one possible implementation of retinal camera 110. The illustrated embodiment of retinal camera 300 includes a two-dimensional sensor array 305, data conversion circuitry 310, a memory buffer 315, an integrated image signal processor (ISP) 320, and an output port 325.

During operation, two-dimensional image data (e.g., retinal images) is acquired by sensor array 305 and converted from the analog domain to the digital domain by data conversion circuitry 310. The image data may be acquired at a high frame rate (e.g., 24, 48, 60, 240, 1000 frames per second) and stored into memory buffer 315. ISP 320 operates on the buffered retinal image frames to identify useable or defect regions, annotate the regions of interest in the image frames, and/or combine the useable regions into high quality, composite retinal images. Accordingly, in one embodiment, some of the image processing tasks described above may be off-boarded to ISP 320 from controller 315. ISP 320 may be considered a logical subcomponent of controller 315.

Figure 4:
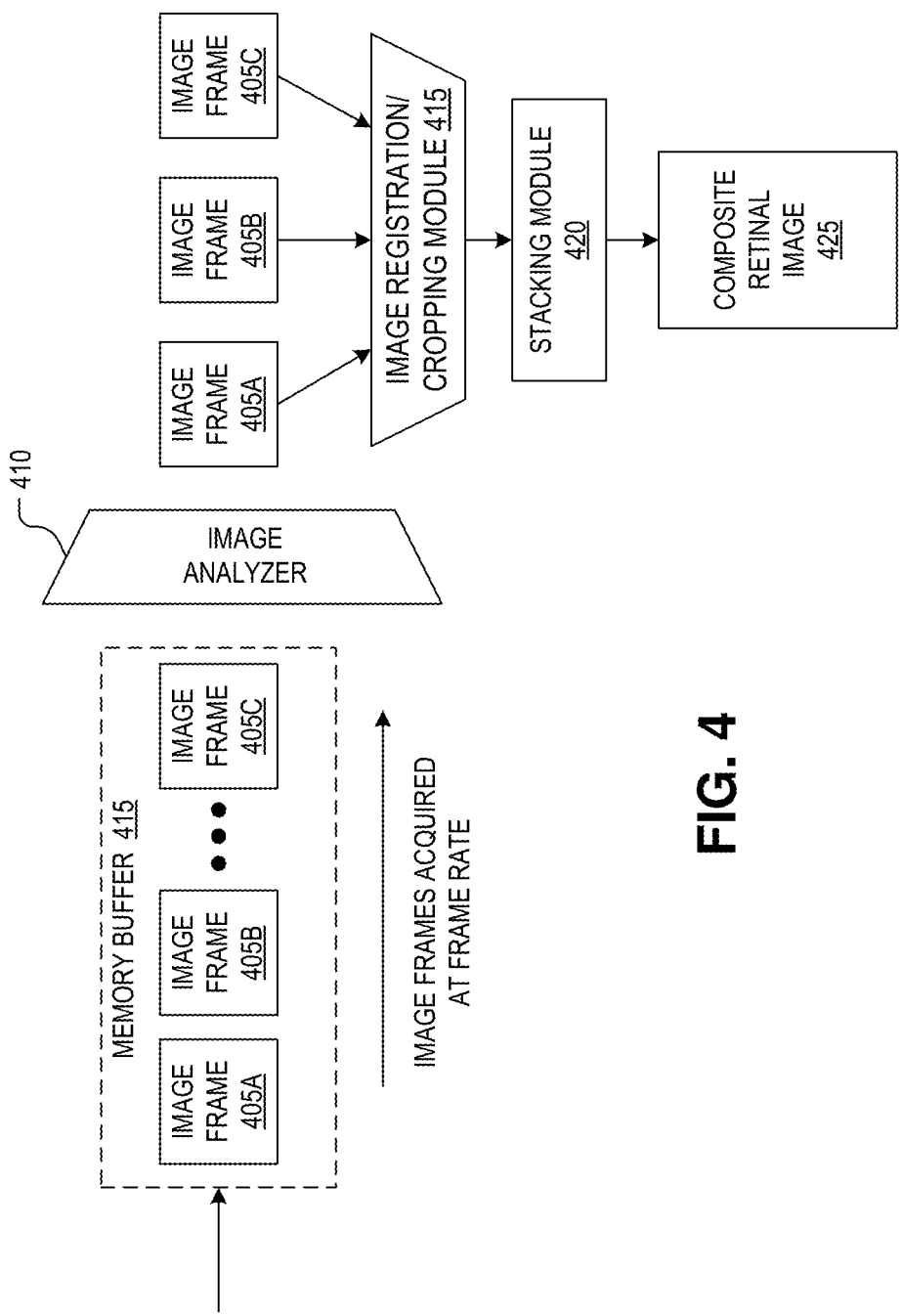
FIG. 4 is a block flow diagram illustrating image processing by a retinal camera including an integrated image signal processor, in accordance with an embodiment of the disclosure.

FIG. 4 is a block flow diagram illustrating image processing by a retinal camera (e.g., retinal camera 300 of FIG. 3) including an integrated image signal processor (e.g., ISP 320 of FIG. 3), in accordance with an embodiment of the disclosure. As illustrated, image frames 405A-C of a retina are acquired by a sensor array (e.g., sensor array 305 of FIG. 3) at a high frame rate, converted into the digital domain by data conversion circuitry (e.g., data conversion circuitry 310 of FIG. 3), and buffered into a memory buffer (e.g., into memory buffer 315 of FIG. 3). An image analyzer 410 is executed by the ISP to analyze the buffered retinal images 405 (a sort of preprocessing) to determine which portions of images frames are of sufficient quality and which are of insufficient quality due to unacceptable image artifacts. For example, image analyzer 410 may analyze image frames 405 for blurred portions, portions that do not have sufficient contrast to be useful, are washed out, and/or include unacceptable corneal or iris reflections, or lens flare. Image portions that are deemed unacceptable are flagged unacceptable (e.g., marked or annotated) while image portions that are deemed acceptable are flagged as such. The image frames are then registered to each other (e.g., pixel-to-pixel alignment), cropped to a common field of view by image registration/cropping module 415, and then combined by stacking module 420 into a single composite retinal image 425. Stacking module 420 may combine images to generate high dynamic range images. In other embodiments, image frames 405 are simply combined without analysis and/or annotation of the individual image frames. All image processing steps and hardware discussed in connection with FIGS. 3 and 4 can be considered part of a "controller" in accordance with the teachings of the present disclosure.

Figure 5:
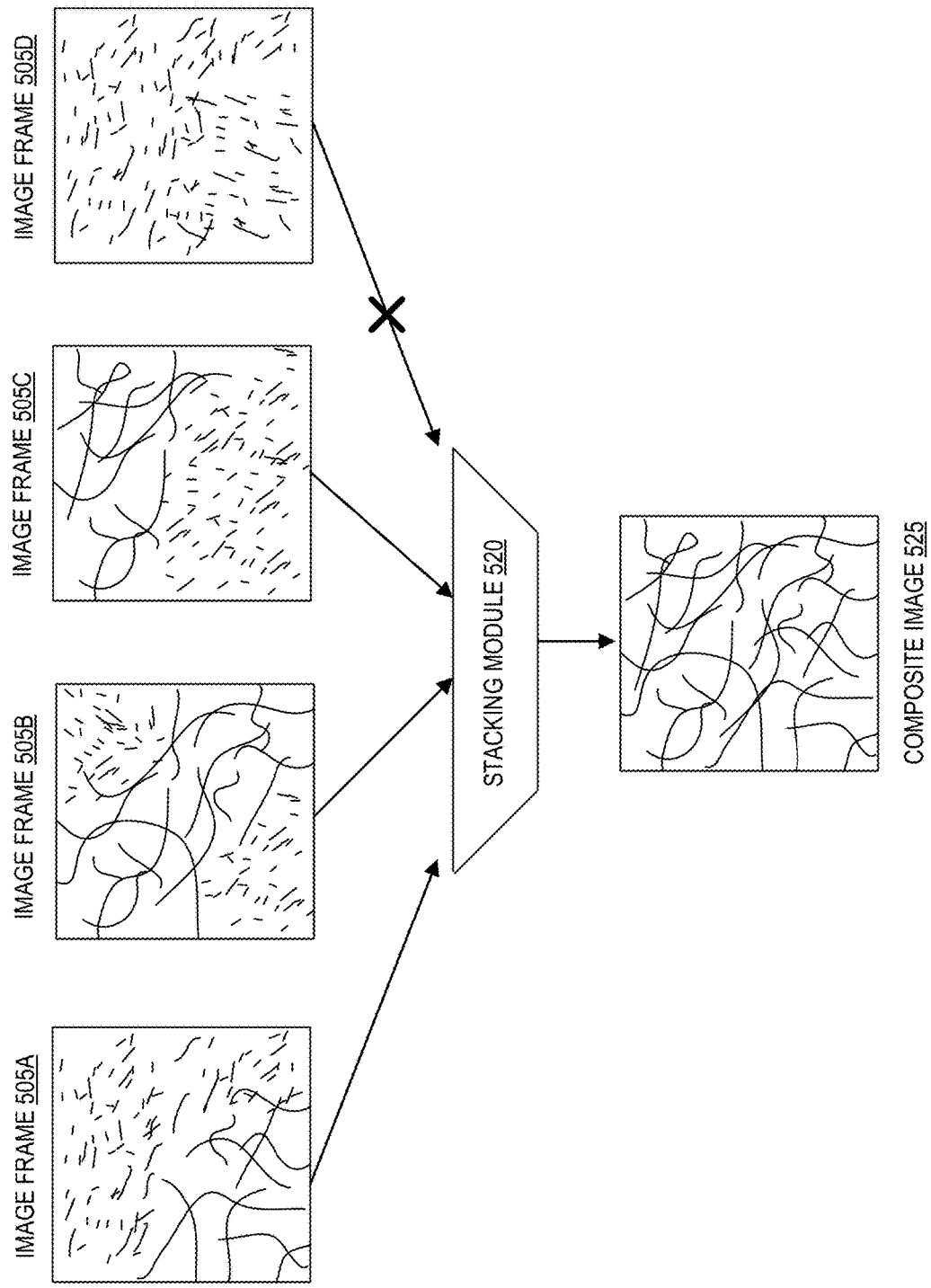
FIG. 5 illustrates focus stacking images of an iris, in accordance with an embodiment of the disclosure.

FIG. 5 illustrates focus stacking images of an iris, in accordance with an embodiment of the disclosure. As shown, four image frames (505A-505D) of a retina are captured with an image sensor. Long lines represent fully resolved veins and other anatomical structures in/on the retina; short dashed lines represent out-of-focus or washed out portions of the image. As shown, the lower left hand corner of image frame 505A is fully resolved, but the rest of the image is not. Similarly, the middle portion (extending from the upper left-hand corner of the frame to the bottom right-hand corner) of image frame 505B is in focus and fully resolved, but the rest of image frame 505B is not. The upper right-hand corner of image frame 505C is in focus, but the rest of the image is not. Lastly, image frame 505D is out of focus and contains no useful information. Accordingly, image frame 505D is removed, and not sent to stacking module 520 for use in composite image 525. The rest of image frames 505A-505C are sent to stacking module 520 to be combined into a single high-resolution composite image 525 with a large depth of field. In one embodiment, images may be combined using edge detection, feature detection, or Fourier analysis.

Figure 6:
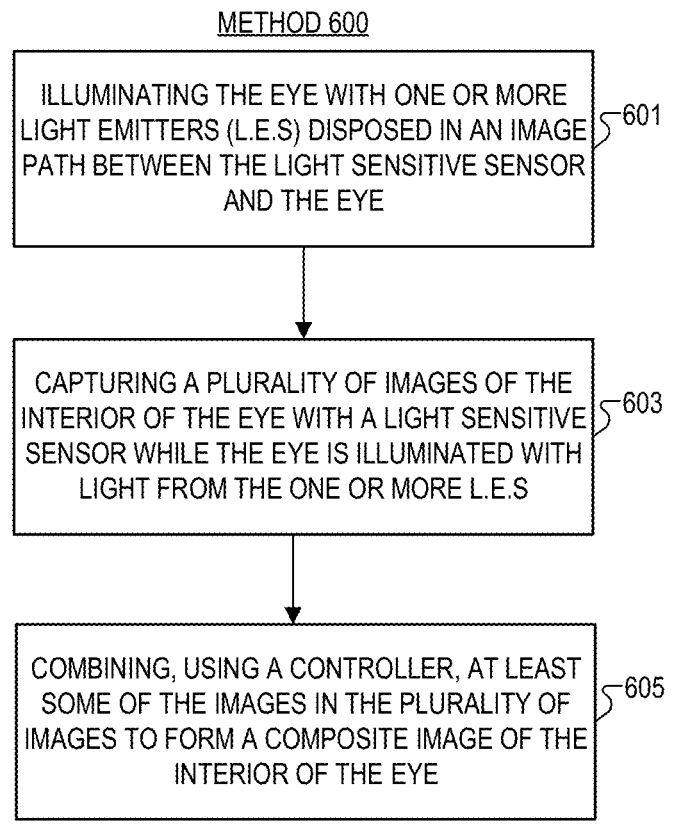
FIG. 6 illustrates a flow chart for a method of imaging an interior of an eye, in accordance with an embodiment of the disclosure.

FIG. 6 illustrates a flow chart for a method 600 of imaging an interior of an eye, in accordance with an embodiment of the disclosure. It is appreciated that blocks (e.g., blocks 601-605) in method 600 may occur in any order and even in parallel. Moreover, blocks maybe added to, or removed, from method 600 in accordance with the teachings of the present disclosure.

Block 601 shows illuminating the eye with one or more light emitters (LEs) disposed in an image path between the light sensitive sensor and the eye during capture of the sequence of images. In some embodiments this may include illuminating the eye from a plurality of positions in the image path. For example, the eye may be illuminated with one or more LEs disposed on one or more arms from a dynamic illuminator disposed in the image path during capture of the plurality of images. In some embodiments, the one or more arms are rotated relative to the eye, and the eye is illuminated with the one or more LEs at the plurality of positions while the one or more arms are rotating. Conversely, the eye may be illuminated from fixed positions in the image path.

Block 603 illustrates capturing a plurality of images of the interior of the eye with a light sensitive sensor while the eye is illuminated with light from the one or more LEs. In one embodiment, the camera may capture images at the same rate as the LEs turn on. Alternatively, the LEs may continuously illuminate the eye during image capture.

Block 605 discloses combining, using a controller, at least some of the images in the plurality of images to form a composite image of the interior of the eye. In some embodiments, this may include at least one of focus stacking, image stitching, image blending, or any combination thereof.

In one embodiment, one or more images in the plurality of images may be excluded from the composite image. The one or more images that are excluded may include at least one of out of focus images, image artifacts, reflections in the image, or objects (e.g., the dynamic illuminator) other than the eye in the image. It is appreciated that a number of techniques to filter out poor quality images may be used. For example, a first set of low quality images may include overexposed images having a luminance value (e.g., an average luminance value across all pixels, or sets of pixels, in the image) greater than a first threshold luminance value, or underexposed images having a luminance value less than a second threshold luminance value. In some embodiments, the images in the first set may not be clearly resolved for other reasons such as the image being too blurry (e.g., because the image sensor moved during capture), the images not containing an image of the retina (e.g., because the subject moved during image capture), or the like. Images may be removed via manual selection or by automated selection (e.g., using high pass/low pass filters to remove images with luminance values that are too high or too low, and/or or using a machine learning algorithm to remove images not including a retina, or the like).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for imaging an interior of an eye, comprising:
 a light sensitive sensor;
 a housing structure with an opening defining an imaging area to place the eye for imaging by the light sensitive sensor;

one or more light emitters (LEs) capable of outputting light, and disposed in an image path between the light sensitive sensor and the imaging area, wherein the one or more LEs are disposed on one or more arms that extend into the image path and obstruct a portion of the image path extending to the light sensitive sensor;

a controller coupled to the one or more LEs, and the light sensitive sensor, wherein the controller implements logic that when executed by the controller causes the apparatus to perform operations including:
illuminating the imaging area with the one or more LEs; and
capturing, with the light sensitive sensor, a plurality of images of the interior of the eye as the eye is illuminated with the light from the one or more LEs.

2. The apparatus of claim 1, wherein the controller further implements logic that when executed by the controller causes the apparatus to perform operations including:
combining at least two images in the plurality of images to form a composite image of the interior of the eye, wherein the combining removes one or more artifacts present in the plurality of images from the composite image, the one or more artifacts due to the one or more arms being present in the image path.

3. The apparatus of claim 2, wherein the controller further implements logic that when executed by the controller causes the apparatus to perform operations including:
excluding one or more images in the plurality of images from the composite image, wherein the one or more images include at least one of out of focus images, image artifacts, reflections in the image, or objects other than the eye in the image.

4. The apparatus of claim 2, wherein the combining includes at least one of focus stacking, image stitching, image blending, or any combination thereof.

5. The apparatus of claim 1, wherein the controller further implements logic that when executed by the controller causes the apparatus to perform operations including:
sequentially illuminating the imaging area with the one or more LEs from a plurality of different positions in the image path.

6. The apparatus of claim 5, wherein the one or more LEs are disposed on a single arm, and wherein the controller further implements logic that when executed by the controller causes the apparatus to perform operations including:
rotating the single arm; and
illuminating the imaging area with the one or more LEs while the single arm is rotating.

7. The apparatus of claim 6, wherein the single arm is attached to a ring and extends toward the center of the ring, and wherein rotating the single arm includes rotating the ring around a pivot point; or
wherein the single arm is rotated around a point of attachment, and wherein the one or more LEs are disposed at a distal end of the single arm opposite the point of attachment.

8. The apparatus of claim 5, wherein the one or more arms are disposed at fixed positions in the image path.

9. The apparatus of claim 8, wherein the one or more arms are a plurality of arms and are disposed on a ring-shaped structure, and wherein at least one of the one or more arms extend towards a center of the ring, and at least one of the one or more arms extend away from the center of the ring.

10. The apparatus of claim 1, wherein at least part of the illumination system is transparent, or capable of becoming transparent.

11. A method of imaging an interior of an eye, comprising:
illuminating the eye with one or more light emitters (LEs) disposed in an image path between a light sensitive sensor and the eye during capture of a plurality of images, wherein the one or more LEs are disposed on one or more structures that extend into the image path and obstruct a portion of the image path extending between the eye to the light sensitive sensor;
capturing a plurality of images of the interior of the eye with the light sensitive sensor as the eye is illuminated with light from the one or more LEs; and
combining, using a controller, at least two of the plurality of images to form a composite image of the interior of the eye.

12. The method of claim 11, wherein combining at least two of the images in the plurality of images to form the composite image includes at least one of focus stacking, image stitching, image blending, or any combination thereof.

13. The method of claim 12, further comprising, excluding one or more images in the plurality of images from the composite image, wherein the one or more images include at least one of out of focus images, image artifacts, reflections in the image, or objects other than the eye in the image.

14. The method of claim 11, further comprising removing an image artifact, caused by the one or more structures holding the one or more light emitters in the image path, from the composite image by at least one of:
excluding portions of the images including the image artifact from being included in the composite image; or
placing the one or more structures in the image path out of focus of the plurality of images.

15. The method of claim 11, wherein illuminating the eye with one or more LEs includes illuminating the eye sequentially from a plurality of different positions in the image path.

16. The method of claim 15, wherein the one or more structures comprise one or more arms.

17. The method of claim 16, further comprising
rotating the one or more arms; and
illuminating the eye with the one or more LEs while the one or more arms is rotating.

18. The method of claim 17, wherein rotating the one or more arms includes at least one of:
rotating a ring around a pivot point, wherein the one or more arms extend towards a center of the ring; or
rotating the one or more arms around a point of attachment, and wherein the one or more LEs are disposed proximate to a distal end of the one or more arms opposite the point of attachment.

19. The method of claim 16, wherein illuminating the eye includes illuminating the eye from fixed positions in the image path.

20. The method of claim 11, wherein at least some of the light reflected from the eye having a path to be incident on the light sensitive sensor is obstructed by the one or more structures.

21. A system for imaging an interior of an eye, comprising:
a housing structure with an opening defining an imaging area to place the eye for the imaging;
an illumination system configurable to illuminate the imaging area from a selected one of directions; and
a light sensitive sensor coupled to capture a plurality of images of the interior of the eye, wherein the illumination system includes a structure that extends into an image path between the light sensitive sensor and the imaging area and obstructs a portion of the image path between the light sensitive sensor and the eye.

22. The system of claim 21, wherein the illumination system includes one or more light emitters (LEs) that sequentially illuminate the imaging area with illumination events.

23. The system of claim 22, wherein:
there are more of the illumination events than images in the plurality of images;
there are fewer of the illumination events than the images in the plurality of images; or
there are the same number of the illumination events as the images in the plurality of images.

24. The system of claim 22, wherein capturing each image in the plurality of images is a discrete occurrence, and each illumination event is a discrete occurrence, and wherein the illumination system illuminates the imaging area from at least two of the directions.

25. The system of claim 21, wherein at least part of the illumination system is transparent, or capable of becoming transparent.

26. The system of claim 21, wherein at least part of the illumination system is in the image path and out of focus.

* * * * *